(12) United States Patent
Marjamaa et al.

(10) Patent No.: US 12,247,353 B2
(45) Date of Patent: Mar. 11, 2025

(54) FIBRE DISSOLUTION WITH ENZYMATIC TREATMENT

(71) Applicant: Teknologian tutkimuskeskus VTT Oy, Espoo (FI)

(72) Inventors: Kaisa Marjamaa, Espoo (FI); Nina Aro, Espoo (FI); Kristiina Kruus, Espoo (FI); Jenni Rahikainen, Espoo (FI)

(73) Assignee: Teknologian tutkimuskeskus VTT Oy, Espoo (FI)

( * ) Notice: Subject to any disclaimer, the term of this patent is extended or adjusted under 35 U.S.C. 154(b) by 1019 days.

(21) Appl. No.: 17/254,317

(22) PCT Filed: Jun. 20, 2019

(86) PCT No.: PCT/FI2019/050486
§ 371 (c)(1),
(2) Date: Dec. 21, 2020

(87) PCT Pub. No.: WO2019/243673
PCT Pub. Date: Dec. 26, 2019

(65) Prior Publication Data
US 2021/0172119 A1    Jun. 10, 2021

(30) Foreign Application Priority Data
Jun. 21, 2018 (FI) ...................... 20185565

(51) Int. Cl.
*D21C 5/00* (2006.01)
(52) U.S. Cl.
CPC .................. *D21C 5/005* (2013.01)

(58) Field of Classification Search
CPC ........ D21C 5/005; C12N 9/0083; C12P 19/04
See application file for complete search history.

(56) References Cited

U.S. PATENT DOCUMENTS

2015/0107789 A1    4/2015  Ni et al.
2016/0369456 A1   12/2016  Flynn et al.
(Continued)

FOREIGN PATENT DOCUMENTS

| EP | 2116557 A1 | 11/2009 |
|---|---|---|
| WO | WO A1 WO2009135875 | 11/2009 |
| WO | WO A1 WO2014130812 | 8/2014 |

OTHER PUBLICATIONS

Berthold et al: An improved method for determination of softwood Kraft pulp molecular mass distribution. 11th International Symposium on Wood and Pulping Chemistry, 2001, pp. 363-366.
(Continued)

*Primary Examiner* — Dennis R Cordray
*Assistant Examiner* — Matthew M Eslami
(74) *Attorney, Agent, or Firm* — Laine IP Oy

(57) ABSTRACT

The present invention concerns a process for the dissolution of cellulose using an enzymatic treatment, followed by a chemical dissolution. Particularly, the invention relates to the utilization of oxidizing enzymes for said enzyme treatment step. The process of the invention will cause an improved dissolution of high molar mass cellulose fibres. The improved dissolution properties also cause an improved reactivity of the cellulose in subsequent reactions.

13 Claims, 6 Drawing Sheets

(56) References Cited

U.S. PATENT DOCUMENTS

2018/0142084 A1* 5/2018 Cathala ............... D21H 11/20
2021/0054567 A1* 2/2021 Flynn ................ D21H 15/10

OTHER PUBLICATIONS

Grönqvist et al: Enhanced pre-treatment of cellulose pulp dissolution into NaOH/ZnO. Cellulose, 2016, vol. 22, pp. 3981-3990.

Hu et al: Enzyme mediated nanofibrillation of cellulose by the synergistic actions of an endoglucanase lytipolysaccharide monooxygenase (LPMO) and xylanase. Scientific Reports, Feb. 16, 2018, vol. 8, pp. 1-8.

Hu et al: Oxidative cleavage of some cellulosic substrates by auxiliary activity (AA) family 9 enzymes influences the adsorption/desorption of hydrolytic cellulase enzymes, Green Chemistry, 2016, vol. 18, No. 23, pp. 6329-6336.

Hu et al: Substrate factors that influence the synergistic interation of AA9 and cellulases during the enzymatic hydrolysis of biomass, Energy & Environmental Science, 2014, vol. 7, No. 7, pp. 2308-2315.

Kapur et al: A New Method for Gray-LEvel Picture Thresholding Using the Entropy of the Histogram, Comput. Vision, Graph. Image Process., 1985, vol. 29, pp. 273-285.

Makelä et al: , Clustered Single Cellulosic Fiber Dissolution Kinetics and Mechanisms through Optical Microscopy under Limited Dissolving Conditions. Biomacromolecules, 2018.

Molinier et al: 3D-Connected Componets Analysis for Traffic Monitoring in Image Sequences Acquired from a Helicopter, Image Analysis: 14th Scandinavian Conference, SCIA 2005, Joensuu, Finland, Jun. 19-22, 2005, Proceedings, 2005, pp. 141-150.

Obolenskaya et al: Laboratory work on the chemistry of wood and cellulose, Ecologia, 1991.

Quintana et al: Cellulose oxidation by laccase-TEMPO treatments. Carbohydrate Polymers, 2017, vol. 157, pp. 1488-1495.

Villares et al: Lytic polysaccharide monooxygenases disrupt the cellulose fibers structure. Scientific Reports, 2017, vol. 7, Article: 40262.

* cited by examiner

FIBRE DISSOLUTION WITH ENZYMATIC TREATMENT

BACKGROUND OF THE INVENTION

Field of the Invention

The present invention concerns a process for enzymatic treatment of cellulose for chemical dissolution. Particularly, the invention relates to the utilization of oxidizing enzymes for said enzyme treatment step.

Description of Related Art

Unmodified cellulose is a molecule with a low solubility in water and with strong hydrogen bonding network, leading to a stabile molecular structure, resistant even to hydrolysis by weak acids and to hydrolytic action of many enzymes. It is a semi-crystalline polymer having amorphous regions as well as crystalline regions. Water causes swelling of the polymer, but does not dissolve it.

The dissolution cellulose thus requires some modification of the structure, either by introducing hydrophilic functional groups into the cellulose structure, or by breaking hydrogen bonds, or by a combination of these alternatives.

Cellulose is typically solubilized in order to facilitate one of the following: the regeneration of cellulose, the chemical modification of cellulose and the degradation of cellulose. Due to the varying requirements of these options (e.g. the regeneration of cellulose and the degradation of cellulose are quite different end-purposes), there is a constant requirement for new methods of causing increased dissolution of cellulose.

A commonly used approach for the dissolution of cellulose is the use of aqueous sodium hydroxide (NaOH). The advantages of this alternative include its low cost, its simple approach, as well as the need for only common, easily handled and non-polluting chemicals. However, the NaOH solution is not capable of effectively dissolving cellulose having a high degree of polymerization.

The use of highly concentrated and aggressive chemical solvents is also not advantageous. Therefore, enzymatic improvement of cellulose dissolution has been studied extensively during recent years.

Lytic polysaccharide monooxygenases (LPMO) are enzymes that can oxidize cellulose. The oxidation occurs at C1 and/or C4 positions, which leads to formation of lactone or ketoaldose, and cleavage of glycosidic linkages. The LPMOs can oxidize and cleave internal linkages in crystalline celluloses, for which hydrolytic endocellulases have impaired activity.

Villares A. et al. (2017) describe the effect of an LPMO treatment on the structure of cellulose. This is, however, merely a pretreatment, which still does not result in dissoluted cellulose. In this publication, LPMOs are said to render the substrate more susceptible to hydrolysis by conventional cellulases.

The use of LPMOs in combination with other enzymes has been described also in Hu, J. et al. (2016), where the effect of the enzyme-induced oxidative cleavage of some cellulose substrates, using said LPMOs, on the adsorption/desorption of hydrolytic cellulose enzymes is described. Likewise, Hu, J. et al (2014) describes the use of similar LPMOs to interact synergistically with cellulases to enhance the enzymatic hydrolysis of a range of cellulosic substrates.

WO2014130812A1 relates to methods of saccharifying a cellulosic material by subjecting the cellulosic material to a cellulolytic enzyme composition and a polypeptide, and optionally a catalase, in the presence of dissolved oxygen.

US20150107789A1, in turn, describes a method of preparing dissolving pulp, including physically separating a kraft pulp or a kraft hydrolysis pulp into first and second fractions, the first fraction having a relatively low lignin content and the second fraction having a relatively high lignin content. The first fibre fraction is subjected to an enzyme treatment with cellulase, xylanase and/or mannanase to decrease viscosity of pulp fraction.

Typically, the use of LPMOs is thus linked to the use of cellulases or other hydrolytic enzymes, and the LPMOs are considered to enhance the total hydrolytic efficiency of the enzyme cocktails.

SUMMARY OF THE INVENTION

The invention is defined by the features of the independent claims. Some specific embodiments are defined in the dependent claims.

According to a first aspect of the present invention, there is provided a process for the dissolution of cellulose, which includes an enzymatic pretreatment step.

According to a second aspect of the present invention, there is provided a process for the dissolution of the cellulose obtained for example from softwood kraft fibres, dissolving grade pulps, recycled fibres or cotton cellulose.

According to a third aspect of the invention, there is provided a process for the enhanced dissolution of cellulose using an oxidizing enzyme, such as the lytic polysaccharide monooxygenase (LPMO) enzyme.

According to a further aspect of the invention, there is provided a use of an oxidizing enzyme, such as the LPMO enzyme for modifying cellulose to improve its dissolution.

The present invention thus relates to a process for the dissolution of cellulose using a pretreatment with oxidizing enzymes.

Several advantages are obtained using the described invention. Among others, the present invention provides an enzymatic process for improving the dissolution of cellulose without causing a significant decrease in the degree of polymerization of the cellulose. The improved dissolution properties also cause an improved reactivity of the cellulose in subsequent reactions.

EMBODIMENTS OF THE INVENTION

Definitions

Figure 1:
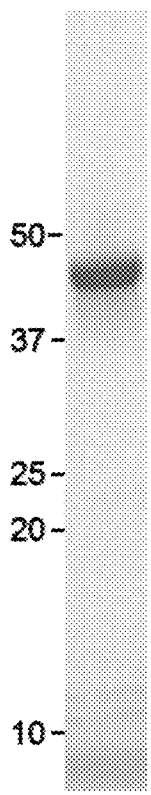
FIG. 1 is an SDS-PAGE image obtained using purified TrAA9A (lane 1) and culture supernatant of *T. reesei* M2182 (lane 2).

In the present context, the "cellulose" material is intended to encompass the fibrous material obtained from a pulping process, particularly the cellulose obtained for example from softwood kraft fibres, dissolving grade pulps, recycled fibres or cotton cellulose.

The term "dissolution" of cellulose is, in turn, intended to describe first the modification of the cellulose into a more soluble form, which in the present context preferably takes place enzymatically, and secondly the actual dissolving step, which in the present context preferably takes place using a solvent.

The present invention thus relates to a process for the dissolution of cellulose fibres, including an enzymatic treatment step, where an oxidative enzyme is utilized, and where the thus obtained enzyme-treated cellulose is subsequently dissolved in an organic solvent.

The cellulose raw material is typically selected from the cellulose obtained for example from softwood kraft fibres, dissolving grade pulps, recycled fibres or cotton cellulose, whereas the oxidative enzyme typically is selected from cellulose oxidizing enzymes, such as monooxygenases, preferably being the lytic polysaccharide monooxygenase (LPMO).

The LPMO is preferably used in a concentration of 0.25-7 mg/g of cellulose raw material, more preferably a concentration of 0.5-6 mg/g, and most suitably a concentration of 1-5 mg/g.

The enzyme treatment typically carried out at ambient conditions, at a pH level of 5-8.

Preferably, the enzyme treatment is continued for 2-24 h.

The oxidative enzyme, i.e. typically the LPMO, can be used in the treatment alone or in combination with other enzymes, including cellobiohydrolases, endoglucanases, xylanases or mannanases. Several different LPMOs can also be used in the treatment simultaneously.

According to a preferred embodiment of the invention, the LPMO possibly utilized as the oxidative enzyme in the present process is obtained from *Trichoderma reesei*, by bioreactor cultivation, followed by purification. Particularly, the enzyme is prepared by overproducing from a strain of *Trichoderma reesei* lacking the genes coding for the major cellulases (cbh1, cbh2, egl, egl2).

The production can be carried out by fermentation for example under cbh1-promoter, on lactose-spent grain extract medium. Preferably, the production is carried out in a synthetic expression system (SES) under *A. niger* 210 core promoter with glucose as carbon source. Typically, a maximum production can be achieved within about 7 days.

According to an embodiment of the invention, the organic solvent used in the dissolution step of the present process is a non-derivatising solvent, such as cupriethylenediamine (CED), preferably used in a concentration of 0.15-0.30M, or NaOH/ZnO, most typically used in concentrations of 18 wt % NaOH and 3.6 wt % ZnO.

Typically, the solvent is used in an amount sufficient to cause complete wetting of the fibres.

According to an embodiment of the invention, the dissolution treatment is carried out at ambient conditions or in sub-zero temperature. The rate of dissolution naturally varies with the amount of raw material to be treated, particularly if a relatively low amount of solvent is used, i.e. an amount causing mere wetting of the raw material. A 95% dissolution of fibre to CED can, however, be achieved within 10 min.

The present invention also relates to the use of an oxidizing enzyme, particularly a lytic polysaccharide monooxygenase (LPMO) in presence of suitable electron donor (e.g. gallic acid, ascorbic acid, lignin, tannin, pigments, cellobiose dehydrohenase, or aryl alcohl oxidase) for modifying cellulose fibres to facilitate their dissolution.

It is to be understood that the embodiments of the invention disclosed are not limited to the particular structures, process steps, or materials disclosed herein, but are extended to equivalents thereof as would be recognized by those ordinarily skilled in the relevant arts. It should also be understood that terminology employed herein is used for the purpose of describing particular embodiments only and is not intended to be limiting.

Reference throughout this specification to one embodiment or an embodiment means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment. Where reference is made to a numerical value using a term such as, for example, about or substantially, the exact numerical value is also disclosed.

As used herein, a plurality of items, structural elements, compositional elements, and/or materials may be presented in a common list for convenience. However, these lists should be construed as though each member of the list is individually identified as a separate and unique member. In addition, various embodiments and examples of the present invention may be referred to herein along with alternatives for the various components thereof. It is understood that such embodiments, examples, and alternatives are not to be construed as de facto equivalents of one another, but are to be considered as separate and autonomous representations of the present invention.

Furthermore, the described features, structures, or characteristics may be combined in any suitable manner in one or more embodiments. In this description, numerous specific details are provided to provide a thorough understanding of embodiments of the invention. One skilled in the relevant art will recognize, however, that the invention can be practiced without one or more of the specific details.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The following non-limiting examples are intended merely to illustrate the advantages obtained with the embodiments of the present invention.

EXAMPLES

Example 1—Production and Purification of the LPMO Enzyme

To construct the expression vector, a fragment containing the gene encoding Cel61A, LPMO enzyme, from *T. reesei* was obtained by PCR from genomic DNA of *T. reesei*. The expression vector was assembled with the yeast recombination cloning method using the PCR fragment and PacI linearized pTTv248 vector backbone. The expression vector contained targeting sequence for the cbh1 locus, cbh1 promoter and terminator and the hphR selection marker. After plasmid rescue and transformation into *E. coli*, the construct was verified by sequencing. The expression cassette was liberated from the expression plasmid B6992 with PmeI restriction enzyme prior to transformation.

To generate the Cel6A producing strain, the M362 strain that is deleted for three major cellulase genes (cbh2, egl1, egl2) was transformed with the expression cassette and grown on MM+hygromycin transformation plates. Transformants were screened first by PCR for 5' and 3' flank integration into the cbh1 locus and absence of the open reading frame for cbh1. The final Cel61A production strain with 4 cellulase deletions was named M1906.

The AA9A from *Trichoderma reesei* was overproduced in *T. reesei* lacking the genes coding for the major cellulases (CBH1, CBH2, EGL1, EGL2). The production was carried out under cbh1-promoter, on lactose (40 g/l)-spent grain extract (20 g/l) medium. The protein production was followed by quantification of soluble protein using BioRad DC kit (BioRad, Hercules, California, USA), preceded by acetone precipitation of the proteins (−20° C., overnight). The composition of the soluble protein was followed by SDS-PAGE analysis using 4-20% gels and BioRad Stain Free Imaging System (BioRad, Hercules, Calif., USA). The bioreactor cultivation was terminated after 7 d and the sample was clarified by centrifugation and concentrated.

Tr AA9A was purified with the following procedure: The concentrated culture supernatant sample was exchanged to buffer 10 mM sodium phosphate pH7 using Sephadex G25 column. Purification continued with anion exchange step with DEAE column using 30 CV long 0-100 mM NaCl gradient. After the first purification step, sample buffer was exchanged to 25 mM sodium acetate pH 5 using ultrafiltration. Final purification step was carried out using HIC column (Phenyl-sepharose). Sample was allowed to bind in 50 mM sodium acetate pH5+0.5 M $(NH_4)_2SO_4$ and elution occurred with 50 mM sodium acetate pH 5. Tr AA9A did not bind the HIC column whereas major contaminating activities were binding. The fractions containing TrAA9A were pooled based on SDS-PAGE analysis and changed to 25 mM sodium acetate pH 5.

The purity of the LPMO preparation was evaluated on SDS-PAGE (see FIG. 1) which allows visualisation of protein bands in the sample. The major band (ca. 45 kDa) in the gel image is TrAA9A whereas only minor low Mw contaminants (10-25 kDa) can be detected from the gel image.

Possible contaminating activities were measured from the sample (Table 1). Very low carboxymethyl cellulose (CMC) activity was detected (10 min incubation at 50° C.) which is indicative of extremely low or non-existing endoglucanase contamination. It is possible that the low CMC activity originates from the LPMO itself which may be capable of low oxidative activity in the absence of electron donor. Similar and very low xylanase and mannanase activities were detected in the purified sample. Xylanase and mannanase activities were measured using Roth xylan from birch wood and Logust bean gum mannan (Sigma) (10 min, pH5, 50° C. for xylanase and 45° C. for mannanase).

TABLE 1

Contaminating (specific) activities in the purified TrAA9A.

| Sample | CMC activity (nkat/mg) | Xylanase activity (nkat/mg) | Mannanase activity (nkat/mg) |
|---|---|---|---|
| TrAA9A purified | 1.2 | 3.2 | 2.6 |

The activity of the purified TrAA9A was further tested with model cellulosic substrate (regenerated amorphous cellulose, RAC) in the presence and absence of electron donor (1 mM gallic acid). The reaction was carried out with 10 mg TrAA9A/g substrate, at 45° C. and pH 7 for 24 h. After LPMO treatment (24 h, 45° C., pH 7), *Agrobacterium* beta-glucosidase (Megazymes, 500 nkat/g cellulose, pH 7) was used to further hydrolyze solubilized neutral and C1 oxidized cello-oligomers to monosaccharides (40° C., 16 h). The sugars were quantified with Dionex ICS-3000 LC device equipped with CarboPac PAD detection. Sugars yields were calculated from released glucose, gluconic acid and cellobionic acid that could be quantified with HPAEC-PAD (Table 2). In the absence of electron donor the amount of sugars released with TrAA9A was under detection limit of the liquid chromatography equipment (<4 mg/L) (Table 2). Thus it may be concluded that the TrAA9A sample is essentially free of endoglucanase. In the presence of 1 mM gallic acid, TrAA9A was found to solubilise 9.5% of the RAC substrate, as indication of LPMO activity.

TABLE 2

Activity of purified TrAA9A (10 mg/g towards regenerated amorphous cellulose (RAC) in the presence and absence of 1 mM gallic acid. After LPMO treatment (24 h, 45° C., pH 7), Agrobacterium beta-glucosidase (500 nkat/g cellulose, pH 7) was used to degrade neutral and C1-oxidised cello-oligomers down to simple sugars (40° C., 16 h). Hydrolysis yields are calculated from released glucose, gluconic acid and cellobionic acid that could be quantified with HPAEC-PAD after the enzyme treatments.

| Sample (batch) | Solubilisation of cellulose yield (%) - no donor | Solubilisation of cellulose (%) - 1 mM gallic acid |
|---|---|---|
| TrAA9A purified | 0.0 | 9.5 |

Example 2—Production the LPMO Enzyme for Fibre Treatment

To construct the expression vectors, fragments containing the gene encoding AA9A, LPMO enzyme, from *T. reesei* were obtained by PCR from genomic DNA of *T. reesei*. Two expression vectors were assembled with the yeast recombination cloning method using the PCR fragments. First one was done to the PacI linearized pTTv248 vector backbone which contained targeting sequence for the cbh1 locus, cbh1 promoter and terminator and the hphR selection marker. The second one was done to the PacI linearized synthetic expression vector B8050 (SES) that contains the *A. niger* 210 core promoter, expression cassette for the synthetic transcription factor, hphR marker and targeting sequence to the cbh1 locus (Rantasalo et al., 2018). After plasmid rescue and transformation into *E. coli*, the constructs were verified by sequencing. The expression cassettes were liberated from the expression plasmids B6992 (construct with cbh1 promoter) and B8183 (SES construct) with PmeI restriction enzyme prior to transformation.

To generate the AA9A producing strains, the M362 strain that is deleted for three major cellulase genes (cbh2, egl1, egl2) was transformed with the expression cassettes and grown on MM+hygromycin transformation plates. Transformants were screened first by PCR for 5' and 3' flank integration into the cbh1 locus and absence of the open reading frame for cbh1. The final AA9A production strain with 4 cellulase deletions were named M1906 (cbh1 promoter) and M2182 (SES construct).

The AA9A from *Trichoderma reesei* was overproduced in *T. reesei* lacking the genes coding for the major cellulases (CBH1, CBH2, EGL1, EGL2). The production was carried out under either by cultivating the M1906 on lactose (40 g/l)-spent grain extract (20 g/l) medium or the M2182 strain on glucose (40 g/l)-yeast extract (10 g/l) medium. The protein production was followed by quantification of soluble protein using BioRad DC kit (BioRad, Hercules, California, USA), preceded by acetone precipitation of the proteins (−20° C., overnight). The composition of the soluble protein was followed by SDS-PAGE analysis using 4-20% gels and BioRad Stain Free Imaging System (BioRad, Hercules, California, USA). The bioreactor cultivation was terminated after 7 d and the sample was clarified by centrifugation and concentrated.

Tr AA9A was purified from the *T. reesei* M1906 culture supernatant with the following procedure: The concentrated culture supernatant sample was exchanged to buffer 10 mM sodium phosphate pH7 using Sephadex G25 column. Purification continued with anion exchange step with DEAE column using 30 CV long 0-100 mM NaCl gradient. After the first purification step, sample buffer was exchanged to 25 mM sodium acetate pH 5 using ultrafiltration. Final purification step was carried out using HIC column (Phenyl-sepharose). Sample was allowed to bind in 50 mM sodium acetate pH5+0.5 M $(NH_4)_2SO_4$ and elution occurred with 50 mM sodium acetate pH 5. Tr AA9A did not bind the HIC column whereas major contaminating activities were binding. The fractions containing TrAA9A were pooled based on SDS-PAGE analysis and changed to 25 mM sodium acetate pH 5.

The purity of the purified LPMO and LPMO in the culture supernatant of *T. reesei* M2182 was evaluated on SDS-PAGE (see FIG. 1) which allows visualisation of protein bands in the sample. The major band (ca. 45 kDa) in the gel image is TrAA9A. Only minor low Mw contaminants (10-25 kDa) were detected from the gel image of the purified protein (FIG. 1, lane 1). The amount of background protein in the culture supernatant of M2182 was also low (FIG. 1, lane 2).

Possible contaminating activities were measured from the purified LPMO and from the M2182 culture supernatant (Table 3). Very low carboxymethyl cellulose (CMC) activity was detected (10 min incubation at 50° C.) in the purified LPMO sample, which is indicative of extremely low or non-existing endoglucanase contamination. It is possible that the low CMC activity originates from the LPMO itself which may be capable of low oxidative activity in the absence of electron donor. Similar and very low xylanase and mannanase activities were detected in the purified sample. Xylanase and mannanase activities were measured using Roth xylan from birch wood and Logust bean gum mannan (Sigma) (10 min, pH5, 50° C. for xylanase and 45° C. for mannanase). The endoglucanase and mannanase activities were under detection limit in the M2182 culture supernatants, whereas ca. 26-54 nka/mg protein of xylanase activity was detected. The data here indicates that also.

TABLE 3

Contaminating (specific) activities in the purified TrAA9A.

| Sample | CMC activity (nkat/mg) | Xylanase activity (nkat/mg) | Mannanase activity (nkat/mg) |
|---|---|---|---|
| TrAA9A purified | 1.2 | 3.2 | 2.6 |
| M2182 culture supernatant | 0 | 26.5-53.4 | 0 |

The activity of the purified TrAA9A was further tested with model cellulosic substrate (regenerated amorphous cellulose, RAC) in the presence and absence of electron donor (1 mM gallic acid). The reaction was carried out with 10 mg TrAA9A/g substrate, at 45° C. and pH 7 for 24 h. After LPMO treatment (24 h, 45° C., pH 7), *Agrobacterium* beta-glucosidase (Megazymes, 500 nkat/g cellulose, pH 7) was used to further hydrolyze solubilized neutral and C1 oxidized cello-oligomers to monosaccharides (40° C., 16 h). The sugars were quantified with Dionex ICS-3000 LC device equipped with CarboPac PAD detection. Sugars yields were calculated from released glucose, gluconic acid and cellobionic acid that could be quantified with HPAEC-PAD (see the above Table 2). In the absence of electron donor the amount of sugars released with TrAA9A was under detection limit of the liquid chromatography equipment (<4 mg/L) (see the above Table 2). Thus it may be concluded that the TrAA9A sample is essentially free of endoglucanase. In the presence of 1 mM gallic acid, TrAA9A was found to solubilise 9.5% of the RAC substrate, as indication of LPMO activity.

The efficiency of the purified LPMO and culture supernatant of M2182 preparations in oxidizing cotton fibres from Whatman n:o 1 filter paper was compared. The cotton fibres (2.5% w/v) were treated with the enzyme (2 mg/g) for 6 h at 45° C. at pH 7 in the presence or absence of 1 mM gallic acid (GA). The generation of new aldehyde groups in pulp was assayed using a colorimetric TTC method (Obolenskaya et al. 1991). The result indicated similar efficiency of both enzyme preparations in cellulose fibre oxidation, indicating that either method can be used for producing the LPMO for fibre treatments (Table 4).

TABLE 4

Aldehyde groups in cotton pulp after treatment with purified Tr AA9A from strain M1906 and unpurified Tr AA9A from strain M2182. The same level of enzyme action was observed with the purified and unpurified enzyme. Tr AA9A action was observed only in the presence of gallic acid (GA).

| Treatment of cotton fibres | Aldehyde goups in pulp (μmol/g) |
|---|---|
| no enzyme, no GA | <14 |
| no enzyme, 1 mM GA | <14 |
| Tr AA9A (M1906), 1 mM GA | 25 |
| Tr AA9A (M1906), no GA | <14 |
| Tr AA9A (M2182), 1 mM GA | 25 |
| Tr AA9A (M2182), no GA | <14 |

Example 3—Treatments of Pulp with TrAA9A

Figure 2:
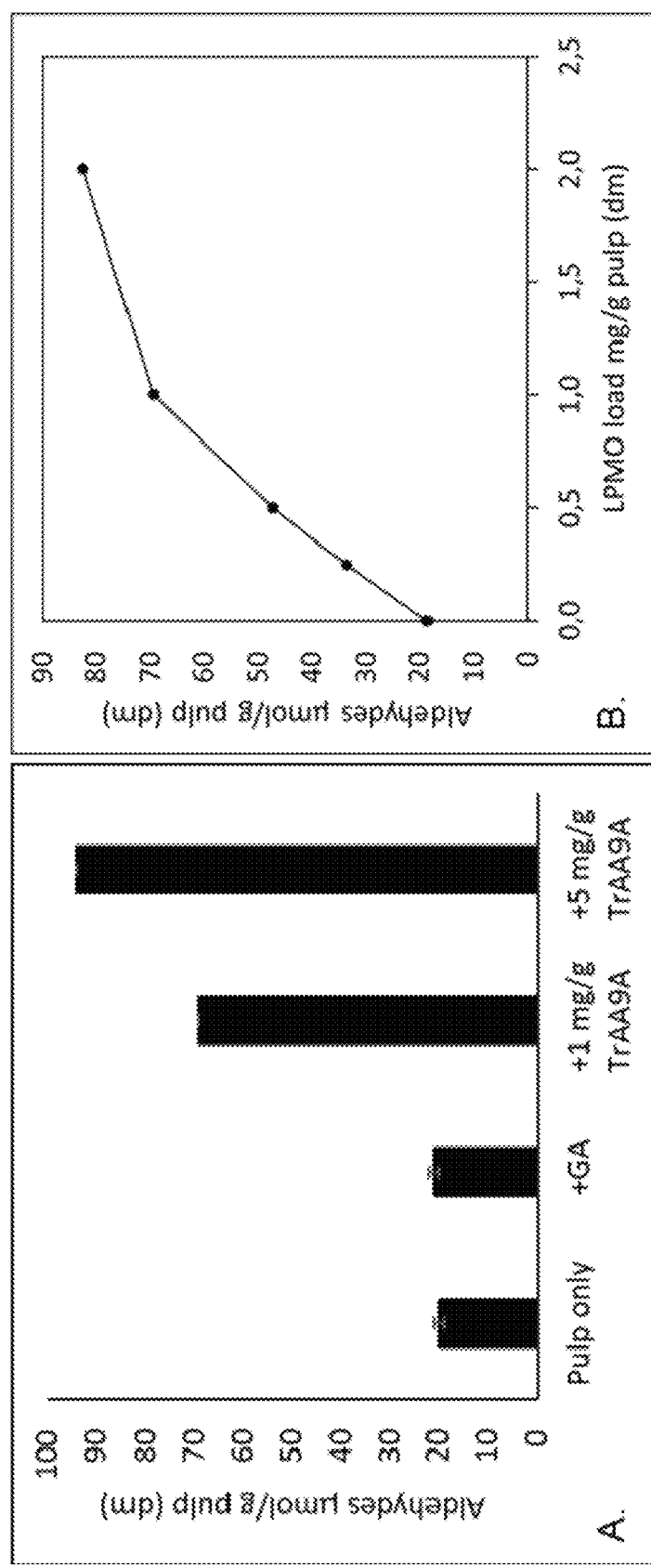
FIG. 2 shows the amount of aldehydes in bleached softwood pulp after treatment with purified Tr AA9A, measured with TTC assay. A) Bleached softwood pulp treated 1 mM gallic acid (GA), with 5 mg TrAA9A/g pulp (DM) or with 1 mM GA and 5 mg TrAA9A/g pulp (DM). B) Bleached softwood pulp treated 1 mM gallic acid (GA) with 0.25-2 mg TrAA9A/g pulp (DM).

Bleached softwood kraft pulp (washed in Na-form) samples were incubated at 3% (dry matter) pulp consistency at 45° C. using 5 mg/g enzyme dosage of purified Tr AA9A and 1 mM gallic acid for 24 h in 50 mM sodium phosphate buffer pH 7. The reference treatments were carried out without the Tr AA9A or gallic acid or using purified Tr Cel45A endoglucanase instead of Tr AA9A. The treatments were carried out in shake flaks under constant impeller mixing. After the treatment the solids were recovered by filtration and thoroughly washed with water prior to TTC assay, CED microscopy and analysis of the molar mass distribution The TTC assay results in FIG. 2A show that that the aldehydes are formed when the LPMO and gallic acid are included in the reaction.

In another experiment, the bleached softwood kraft pulp (washed in Na-form) was incubated at 20% (dry matter) pulp consistency at 45° C. using 1 mg/g enzyme dosage of purified Tr AA9A and 5 mM gallic acid for 6 h in 50 mM sodium phosphate buffer pH 7. A reference treatment was carried out without the Tr AA9A. The treatments were carried out in Farinograph with constant mixing. After the treatment the solids were recovered by filtration and thoroughly washed with water prior to viscosity measurement and alkaline solubility test.

In a third experiment, the bleached softwood kraft pulp (washed in Na-form) samples were incubated at 3% (dry matter) pulp consistency at 45° C. using 0.25-2 mg/g enzyme dosage of purified Tr AA9A and 1 mM gallic acid for 24 h in 50 mM sodium phosphate buffer pH 7. The treatments were carried out in shake flaks under constant impeller mixing. After the treatment the solids were recovered by filtration and thoroughly washed with water prior to TTC assay (Obolenskaya et al. 1991). The results in the FIG. 2B show and that the amount of formed aldehydes is dependent on LPMO dosage.

Figure 3:
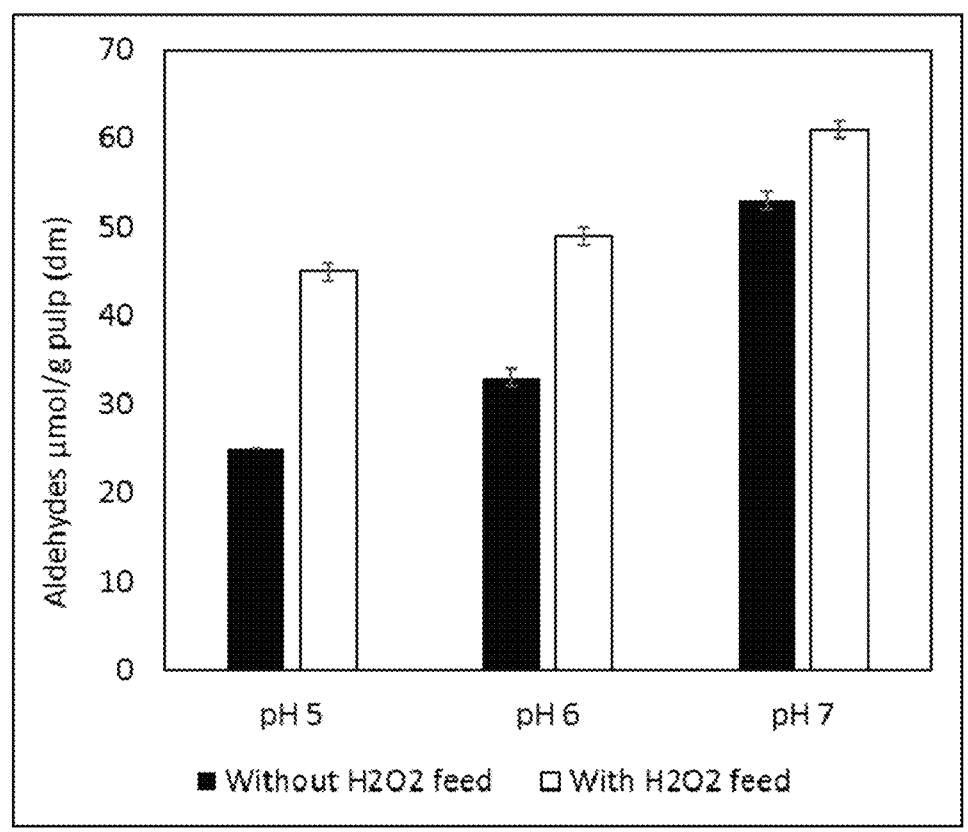
FIG. 3 shows the effect of reaction pH and hydrogen peroxide on the amount of aldehydes in bleached softwood pulp after treatment with purified Tr AA9A, measured with TTC assay.

In a fourth experiment effect reaction pH and addition of hydrogen peroxide on the LPMO oxidation efficiency was studied. The bleached softwood kraft pulp (washed in Na-form) samples were incubated at 3% (dry matter) pulp consistency at 45° C. using 5 mg/g enzyme dosage of purified Tr AA9A and 1 mM gallic acid for 6 h in 50 mM sodium phosphate buffer pH 7, 50 mM sodium phosphate buffer pH 6 or 50 mM sodium acetate buffer pH 5. The same experiments were carried also with addition of 0.1 mM hydrogen peroxide/h to the reaction. The reaction efficiency was followed by measuring pulp aldehydes with the TTC assay (Obolenskaya et al 1991). The data in FIG. 3 shows that addition of hydrogen peroxide enhances reaction efficiency especially at pH 5 and pH 6.

Figure 4:
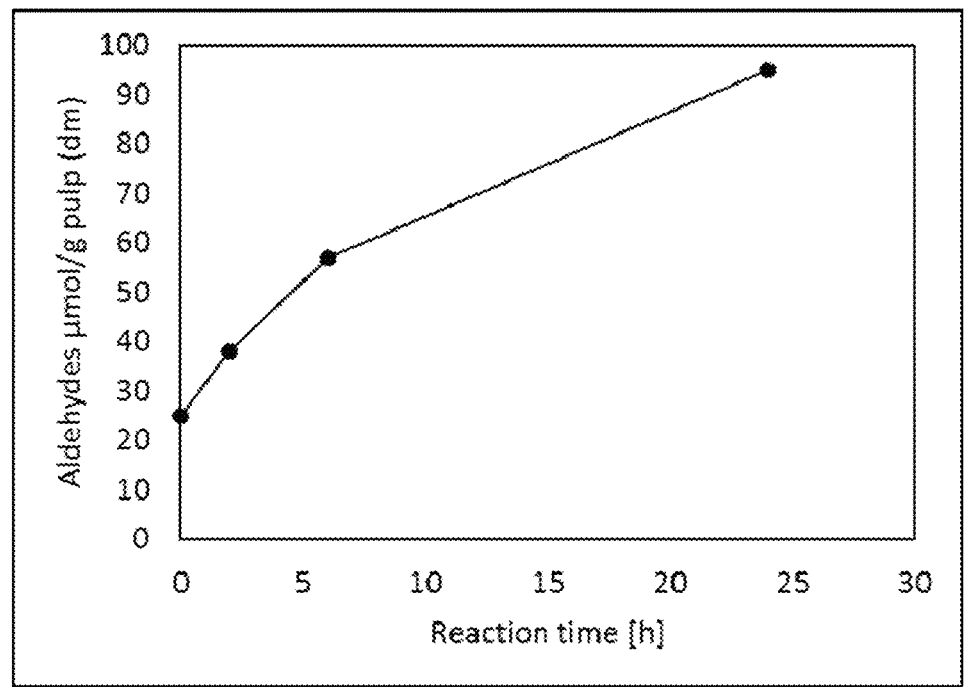
FIG. 4 shows the effect of reaction time on the amount of aldehydes in bleached softwood pulp after treatment with purified Tr AA9A, measured with TTC assay.

In a fifth experiment, effect of reaction time on the formation of aldehydes was studied. The bleached softwood kraft pulp (washed in Na-form) samples were incubated at 3% (dry matter) pulp consistency at 45° C. using 5 mg/g enzyme dosage of purified Tr AA9A and 1 mM gallic acid for 2, 6 or 24 h. The formation of aldehydes was followed by measuring pulp aldehydes with the TTC assay (Obolenskaya et al 1991) (FIG. 4).

Example 4—CED Microscopy

The effect of LPMO treatment with Tr AA9A on fibre dissolution properties was studied with a microscopy-based method (Makela et al 2018).

A small sample of fibres was dispersed in water and a droplet containing dozens of fibres was placed on a glass slide and allowed to dry at 30° C. Ca. 20 fibres, representing the total sample, were selected for dissolution. For each dissolution, 2-3 fibres were selected and placed on a microscopy slide and covered with a cover slip. Imaging was carried out using a Zeiss Axiolmager M.2 microscope (Carl Zeiss GmbH, Göttingen, Germany). A drop of aqueous 0.2 M cupri-ethylenediamine (CED; Oy FF-Chemicals Ab, Haukipudas, Finland) was added between the microscopy slides and the solution reached the fibres due to capillary effect caused by the space between the microscopy slide and the cover slip. A transmission image was captured after the CED solution addition every 1.0 s using time series mode until the fibre finally was dissolved. The images were either with 2.5× objective (Zeiss EC Plan-Neofluar, numerical aperture of 0.085, Zeiss) or with 5× objective (EC Plan-Neofluar, numerical aperture of 0.16, Zeiss) and polarizer in the angle of 75°. Micrographs were obtained using a Zeiss Axiocam 506 CCD colour camera (Zeiss) in black and white mode and the Zen imaging software (Zeiss). At least twenty fibres per sample were analysed.

Figure 5:
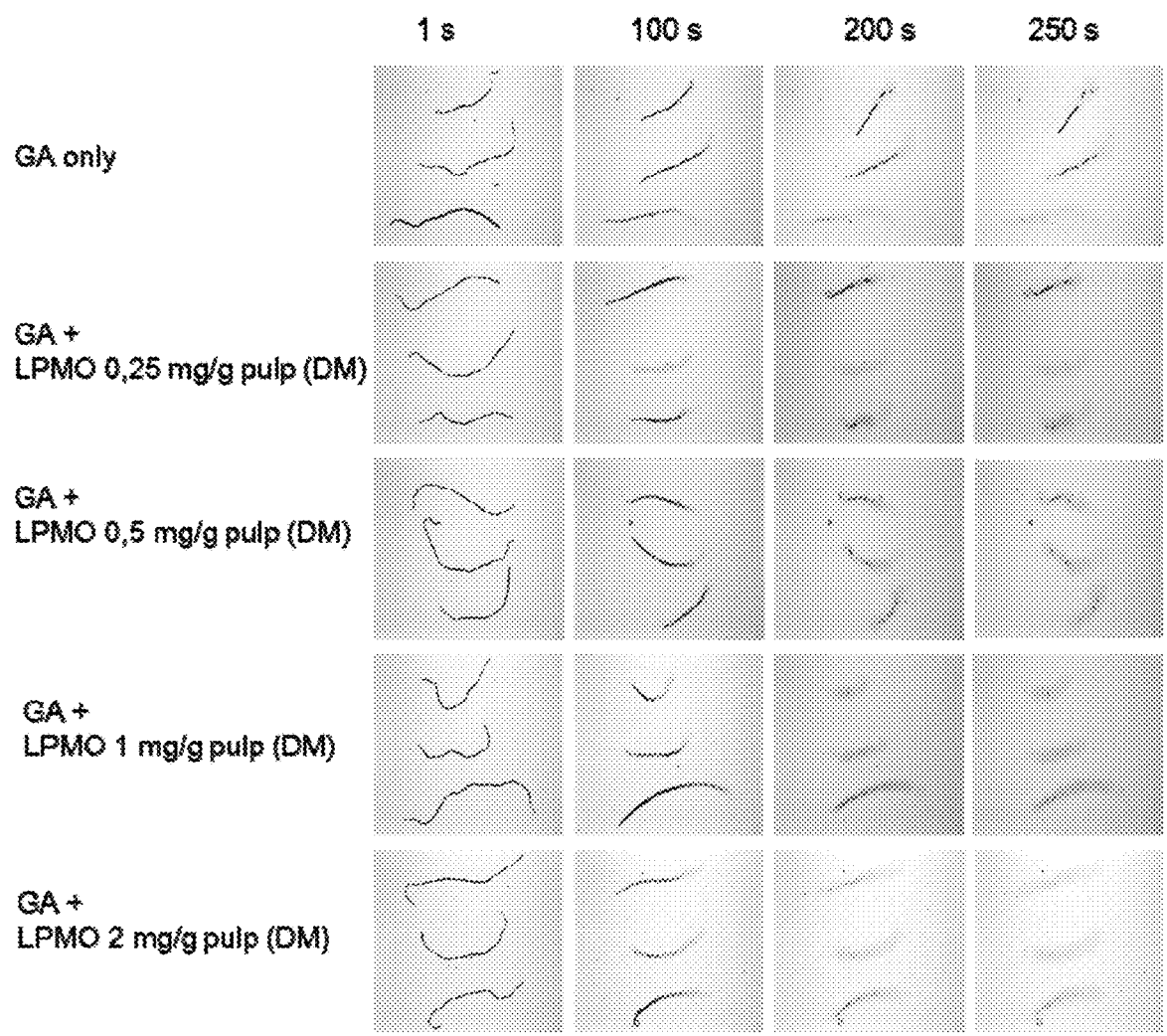
FIG. 5 shows microscopic images of bleached softwood pulp fibres, treated with different dosages of TrAA9A, during dissolution in CED.

FIG. 5 shows microscopic images of softwood pulp fibres treated with different dosages of LPMO at different dissolution time-points, indicating differences in the dissolution rates.

The length and 2D/projectional area of the fibres before and after wetting with CED was estimated using a custom Matlab program. Fibre dissolutions rates were calculated using these parameters. The fibre dissolution microscopy data was also used to determine how the different treatments affected the fibre surface fibrillation and the dissolution mechanism. The dissolution videos representing circa twenty individual fibres of each sample were analysed using automatic image and video processing methods.

As a pre-processing step, images before wetting with CED were discarded automatically by analysing the sum of pixel-wise second derivative along time between consecutive images. The absolute minimum was consistently reached when the microscopy slides were uniformly wetted with CED. Then, each frame of the video after wetting was binarized using a maximum entropy threshold, which maximizes information between objects and the background (Kapur et al 1985). The objects were detected in binary images using 8-connected component analysis (Molinier et al 2005), then assigned a unique label and their corresponding area. The fiber tracking procedure was initialized by selecting the N largest objects in the first image, with N the number of fibres indicated as metadata by the microscope operator. The fibres were then tracked using a spatio-temporal consistency criterion inspired from (Molinier et al 2005), that allowed to match candidate fibres in the current binary image with fibres tracked in the previous images, while simultaneously filtering out other objects (occasional non-fibrous material, air bubbles and other artefacts).

Using these methods, the fibre area (in amount of pixels and $\mu m^2$) was tracked during the dissolution process, and dissolution time curves were obtained for each fibre. The dissolution time at which 95% of the fibre area was dissolved was the single most important parameter but the data could be processed into different clustering models, or dissolution speed gradients etc, which visualised different aspects of the fibre dissolution mechanism.

Figure 6:
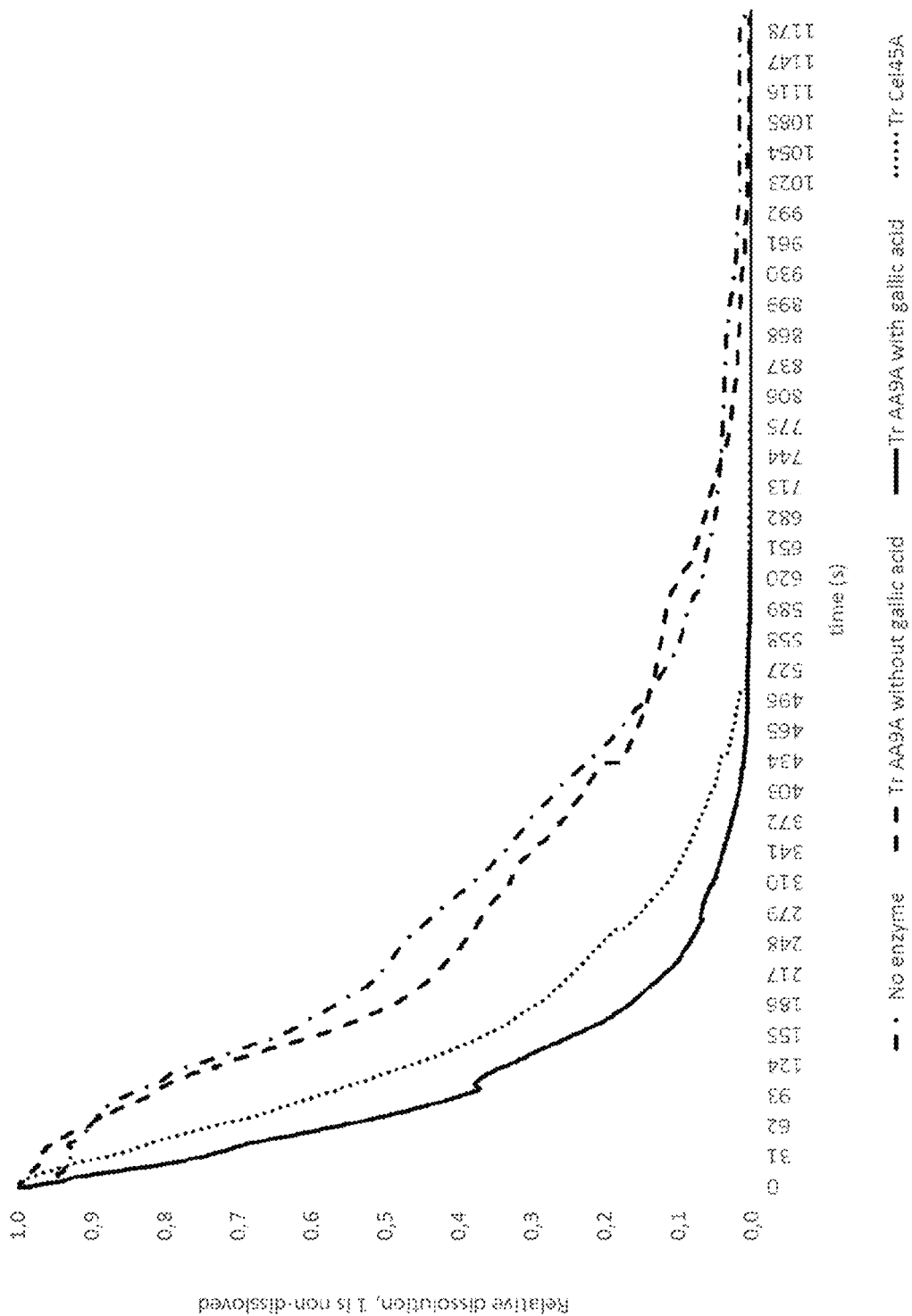
FIG. 6 illustrates the averaged dissolution kinetics of 23 fibres of enzyme-treated fibres, as well as a reference sample treated in the absence of enzyme, whereby the fibre dissolution in 0.2M CED was followed under light microscope, and the image data was converted to numerical form using computational methods.

Averaged dissolution traces of the fibres in one sample are shown in FIG. 6. LPMO treatment was shown to speed-up dissolution of softwood kraft fibres significantly compared to the reference sample. 95% dissolution of enzyme treated fibres was reached in 500 seconds whereas for the reference sample the equal level of dissolution took 900 seconds.

Example 5—Analysis of Molecular Weight Distribution with Size-Exclusion Chromatography For the molar mass measurements, the solid samples were dissolved in DMAc/8% LiCl according to the solvent exchange method described by Berthold et al (2001). The described method includes activation of the sample with water, solvent exchange with methanol and DMAc, followed by ethyl isocyanate derivatisation assisted dissolution into DMAc/8% LiCl. Two replicates of each sample were dissolved. After complete dissolution, the samples were diluted with DMAc providing final LiCl concentration of 0.8% as in the eluent. The samples were filtered (0.45 μm) before the measurement. The SEC measurements were performed using 2×PL gel MiniMixed A columns with a precolumn in DMAc/0.8% LiCl eluent (0.36 ml/min, T=80° C.). In all cases, the elution curves were detected using Waters 2414 Refractive index detector. The molar mass distributions (MMD) were calculated against 8× pullulan (6 100-708 000 g/mol) standards, using Waters Empower 3 software.

The SEC analysis indicated that the LPMO treatment with Tr AA9A in presence of gallic acid as electron donor resulted in clearly lower decrease in molar mass average than the endoglucanase treatment with Tr Cel45A (Table 5).

TABLE 5

Molar mass averages of the bleached softwood pulp treated TrAA9A and reference samples.

| Sample | Mn | Mw | Polydispersity |
|---|---|---|---|
| No enzyme | 71603 | 629103 | 8, 9 |
| TrAA9A only | 68622 | 676541 | 9, 9 |
| TrAA9A with gallic acid | 55279 | 507515 | 9, 3 |
| TrCel45A | 40001 | 356903 | 9, 1 |

Example 6—Viscosity Measurement

The intrinsic viscosity of the pulp was determined by a standard ISO 5351-1 using PSL Rheotek equipment. The limiting viscosity number of cellulose is determined in dilute cupri-ethylene-diamine (CED) solution. First the pulp sample is continuously shaken in flask containing deionized water and copper pieces until the sample has been completely disintegrated. Then the CED solution is added and shaking is continued until the sample has been dissolved. After this the efflux time of the sample is determined with viscometer. The measurement programme of the viscometer gives automatically the intrinsic viscosity value of the sample The treatment of the bleached softwood pulp with Tr AA9A resulted in minor decrease in pulp viscosity (Table 6).

TABLE 6

Viscosities of the bleached softwood pulp samples (20% dry matter consistency) treated with Tr AA9A (1 mg/g pulp (dry matter)) in presence of 5 mM gallic acid and a reference sample treated without the enzyme.

| Sample | Viscosity ml/g |
|---|---|
| Treated without enzyme | 670 |
| Treated with Tr AA9A (1 mg/g pulp (dry matter)) | 600 |

Example 6—Dissolution

Figure 7:
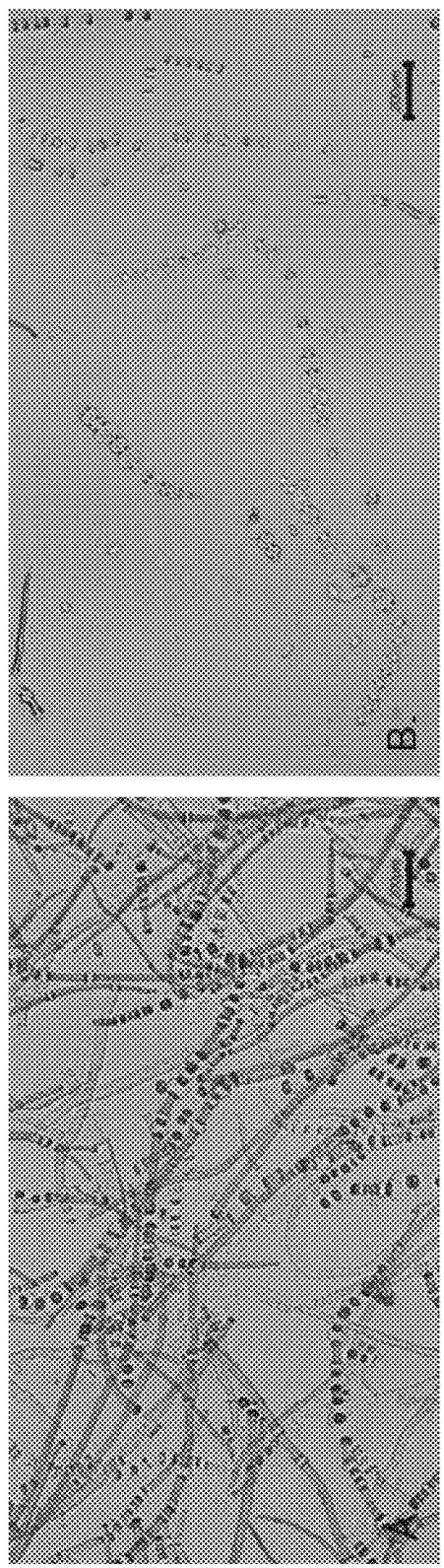
FIG. 7 shows the effect of Tr AA9A treatment on dissolution of bleached softwood pulp in ZnO—NaOH as microscopic images. A) Pulp treated with gallic acid only B) Pulp treated with gallic acid and Tr AA9A.

The bleached softwood pulp treated with Tr AA9A (1 mg/g pulp) and a reference pulp sample treated without enzyme were tested in dissolution in NaOH (6.5 wt %)-ZnO (1.2 wt wt %) in pulp concentrations 2.5 and 3%, respectively, using a method described in WO2009/135875A1. The Tr AA9A treatment enhanced the solubility of pulp, seen as lower amount of undissolved fibres in the microscopy images (FIG. 7A: pulp treated without enzyme, FIG. 7B: pulp treated with Tr AA9A) and increased ball viscosities of the cellulose solutions (Table 7).

TABLE 7

Ball viscosities of cellulose solutions in ZnO—NaOH prepared from bleached softwood pulps treated (6 h, pH 7, 45° C.) at high consistency (20%) without enzyme and with Tr AA9A (LPMO, 1 mg/g pulp).

| Sample | Cellulose concentration % | Ball viscosity s/5 cm (24.5° C.) |
|---|---|---|
| No enzyme | 2.5 | 4.7 |
| LPMO | 3.0 | 27.3 |

INDUSTRIAL APPLICABILITY

The present process can be used to improve the dissolution of cellulose, and generally for replacement of either conventional chemical processes, utilizing harsh conditions, or conventional enzymatic processes, attacking mainly the easily accessed parts of the cellulose, resulting in the hydrolysis of the cellulose linkages and a shortening of the cellulose chain.

Thus, the present process is useful in providing dissoluted high DP cellulose fibres.

Abbreviations
CED cupri-ethylenediamine
DP degree of polymerization
LPMO lytic polysaccharide monooxygenase (LPMO)

CITATION LIST

Patent Literature

WO2014130812A1
US20150107789A1
WO 2009/135875A1

Non-Patent Literature

F. Berthold, K. Gustafsson, E. Sjöholm and M. Lindström, 11$^{th}$ International symposium on wood and pulping chemistry, 2001, pp. 363-366.

J. Hu, V. Arantes, A. Pribowo, K. Gourlay and J. N. Saddler, Energy & Environmental Science, 2014, 7(7), pp. 2308-2315.

J. Hu, A. Pribowo and J. N. Saddler, Green Chemistry, 2016, 18(23), 6329-6336.

J. N. Kapur, P. K. Sahoo and A. K. C. Wong, Comput. Vision, Graph. Image Process., 1985, 29, 273-285.

M. Molinier, T. Häme and H. Ahola, Image Analysis: 14$^{th}$ Scandinavian Conference, SCIA 2005, Joensuu, Finland, Jun. 19-22, 2005, Proceedings, eds. H. Kalviainen, J. Parkkinen and A. Kaarna, Springer Berlin Heidelberg, Berlin, Heidelberg, 2005, pp. 141-150.

V. Mäkelä, R. Wahlström, U. Holopainen-Mantila, I. Kilpeläinen A. W. T. King, Biomacromolecules, 2018, DOI: 10.1021/acs.biomac.7b01797

A. Villares, C. moreau, C. Bennati-Granier, S. Garajova, L. Foucat, X. Falourd, B. Saake, J.-G. Berrin & B. Cathala, Scientific Reports, 2017, 7, 40262

A. V. Obolenskaya, Z. P. Elnitskaya and A. A. Leonovitch, A, 1991, Ecologia. Moscow

The invention claimed is:

1. A process for the dissolution of cellulose fibres comprising:
   subjecting a cellulose raw material to an enzymatic treatment step using a lytic polysaccharide monooxygenase (LPMO) as an oxidative enzyme; and
   dissolving the thus obtained enzyme-treated cellulose in a non-derivatising solvent, wherein the LPMO is used at a concentration of 0.25-7 mg/g of the cellulose raw material in the enzymatic treatment step, and
   wherein the enzymatic treatment step is carried out in the presence of an electron donor,
   wherein the electron donor is gallic acid, and wherein the gallic acid is provided at a concentration of 1-5 mM in the enzymatic treatment step.

2. The process of claim 1, wherein the cellulose raw material is selected from softwood kraft fibres, dissolving grade pulps, recycled fibres or cotton cellulose.

3. The process of claim 1, further comprising carrying out the enzyme treatment at ambient conditions, at a pH level of 5-8, and for 0.5-24 h.

4. The process of claim 1, further comprising carrying out the enzyme treatment in the presence of oxygen, hydrogen peroxide, or both.

5. The process of claim 1, further comprising selecting the non-derivatising solvent from those containing one or more metal ligands.

6. The process of claim 1, further comprising using the solvent in an amount sufficient to cause wetting of the cellulose fibres.

7. The process of claim 1, further comprising carrying out the dissolution treatment, using the non-derivatising solvent, at ambient conditions or sub-zero temperatures for a duration of 10 minutes or more.

8. The process of claim 1, wherein the concentration of LPMO is 0.5-6 mg/g of cellulose raw material.

9. The process of claim 1, wherein the concentration of LPMO is 1-5 mg/g of cellulose raw material.

10. The process of claim 1, wherein the solvent comprises one or more metal ligands selected from the group consisting of copper, cadmium, lithium, and zinc.

11. The process of claim 1, wherein the solvent comprises cupriethylenediamine (CED) or NaOH/ZnO.

12. The process of claim 1, wherein the (LPMO) LPMO produced from a strain of *Trichoderma reesei* lacking genes encoding for cbh1, cbh2, egl1, and egl2.

13. The process of claim 1, wherein the solvent comprises cupriethylenediamine (CED).

* * * * *